US00PP12311P2

(12) United States Plant Patent
Salmon

(10) Patent No.: US PP12,311 P2
(45) Date of Patent: Dec. 25, 2001

(54) BRACTEANTHA PLANT NAMED 'FLORABELLA PINK'

(75) Inventor: Alexander David Salmon, Gapsted (AU)

(73) Assignee: Outback Plants Pty. Ltd., Victoria (AU)

( * ) Notice: Subject to any disclaimer, the term of this patent is extended or adjusted under 35 U.S.C. 154(b) by 19 days.

(21) Appl. No.: 09/740,534

(22) Filed: Dec. 20, 2000

(51) Int. Cl.[7] ..... A01H 5/00
(52) U.S. Cl. ..... Plt./359
(58) Field of Search ..... Plt./359

(56) References Cited

PUBLICATIONS

GTITM UPOVROM Citation for 'Florabella Pink' as per CA PBR 99–1999; Dec. 20, 1999.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct culitvar of *Bracteantha bracteata* named 'Florabella Pink', characterized by its upright, outwardly spreading and rounded plant form; compact plant habit; small lanceolate leaves; pink and white bi-colored involucral bracts and yellow-colored disc florets; and short peduncles that hold inflorescences above the foliage.

1 Drawing Sheet

BACKGROUND OF THE INVENTION

The present invention relates to a new and distinct cultivar of Bracteantha plant, botanically known as *Bracteantha bracteata* and referred to by the cultivar name 'Florabella Pink'.

The new Bracteantha is a product of a planned breeding program conducted by the Inventor in Gapsted, Victoria, Australia. The objective of the program is to create and develop Bracteantha cultivars with a compact growth habit, small leaves, numerous inflorescences, bright involucral bract colors, and short peduncles.

The new Bracteantha originated from a cross by the Inventor of an unidentified yellow involucral bract-colored proprietary selection of *Bracteantha bracteata* as the female, or seed, parent with an unidentified white involucral bract-colored proprietary selection of *Bracteantha bracteata* as the male, or pollen, parent. The new Bracteantha was discovered and selected by the Inventor as a plant within the progeny of the stated cross in a controlled environment in Gapsted, Victoria, Australia in 1997. The selection of the new Bracteantha was based on its growth habit, leaf size, unique involucral bract-coloration and peduncle length as plants of the new Bracteantha are more compact, have smaller leaves, have pink and white bi-colored involucral bracts, and shorter peduncles than plants of the parent selections.

Asexual reproduction of the new Bracteantha by terminal cuttings taken in a controlled environment in Gapsted, Victoria, Australia, has shown that the unique features of this new Bracteantha are stable and reproduced true to type in successive generations.

The new Bracteantha has not been observed under all possible environmental conditions. The phenotype may vary somewhat with variations in environment such as temperature, daylength, light intensity, photoperiod, and water and nutritional status without, however, any variance in genotype.

The following characteristics have been repeatedly observed and are determined to be basic characteristics of 'Florabella Pink' and distinguish the new Bracteantha as a new and distinct cultivar:

1. Upright, outwardly spreading and rounded plant form.
2. Compact plant habit.
3. Small lanceolate leaves.
4. Pink and white bi-colored involucral bracts and yellow-colored disc florets.
5. Short peduncles that hold inflorescences above the foliage.

Plants of the new Bracteantha differ from its sibling cultivars, 'Florabella Gold', U.S. Plant patent application Ser. No. 09/740,532, and 'Florabella White', U.S. Plant patent application Ser. No. 09/740,535 primarily in involucral bract coloration.

The new Bracteantha can be compared to the *Bracteantha bracteata* cultivar 'Nullabor Spectrum', disclosed in U.S. Plant patent application Ser. No. 08/938,583 (abandoned). In side-by-side comparisons conducted by the Inventor in Gapsted, Victoria, Australia, plants of the new Bracteantha are more compact, have shorter and narrower leaves and have slightly smaller inflorescences than plants of 'Nullabor Spectrum'.

The new Bracteantha can also be compared to the *Bracteantha bracteata* cultivar 'Pink Sunrise', not patented. In side-by-side comparisons conducted by the Inventor in Gapsted, Victoria, Australia, plants of the new Bracteantha are taller, have shorter and narrower leaves, and brighter pink involucral bract coloration than plants of 'Pink Sunrise'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Bracteantha. The photograph comprises a side perspective view of a typical plant of 'Florabella Pink' in a container.

DETAILED BOTANICAL DESCRIPTION

The following observations, measurements and values describe plants grown in Gapsted, Victoria, Australia, under outdoor conditions with day temperatues ranging from 15 to 40° C., night temperatures ranging from 8 to 25° C., and light levels ranging from 5,000 to 9,000 foot candles. Rooted liners of the new Bracteantha were planted in 15-cm containers and grown for about 8 to 10 weeks. Color references are made to The Royal Horticultural Society Colour Chart except where general terms of ordinary dictionary significance are used.

Classification:

*Botanical.*—*Bracteantha bracteata* cultivar 'Florabella Pink'.

Parentage:

*Male or pollen parent.*—Unidentified white involucral bract-colored selection of *Bracteantha bracteata*, not patented.

*Female or seed parent.*—Unidentified yellow involucral bract-colored selection of *Bracteantha bracteata*, not patented.

Propagation:

*Type.*—By cuttings.

*Time to initiate roots.*—Summer: About 10 to 20 days at temperatures of 20 to 25° C. Winter: About 15 to 35 days at temperatures of 20° C.

*Root description.*—Fine to fibrous, freely branching.

Plant description:

*General appearance.*—Upright, outwardly spreading and rounded herbaceous plant with lanceolate foliage and inflorescences held above the foliage on short peduncles. Appropriate for 15 pots to 25-cm hanging basket containers.

*Crop time.*—Moderately fast growth rate; to produce a finished 15-cm containerized plant from rooted cuttings, about 8 to 10 weeks are required depending on temperature and light level.

*Plant height.*—About 30 to 45 cm from soil level to top of inflorescences.

*Plant width.*—*About* 35 to 45 cm.

*Branching.*—Moderate, removal of terminal apex enhances branching; typically about 5 to 12 lateral branches per plant.

*Lateral branch description.*—Length: About 10 to 25 cm. Width: About 4 to 7 mm. Internode length: About 0.9 to 3.7 cm. Texture: Slightly pubescent; sometimes with very faint ridges. Color: 143C.

*Foliage description.*—Arrangement: Alternate, single. Quantity: About 22 to 57 per lateral branch. Shape: Lanceolate to broadly linear. Margin: Entire; flat or slightly recurved. Apex: Acute. Base: Decurrent, clasping. Length: About 3.4 to 14.6 cm. Width: About 0.8 to 2.5 cm. Texture: Thin; slightly rough; moderately pubescent on both surfaces. Color: Young leaves, upper surface: 147A. Young leaves, lower surface: 147B. Fully mature leaves, upper surface: 147A, venation, 144B. Fully mature leaves, lower surface: 147B; venation, 144A.

Flowering description:

*Inflorescence form.*—Daisy-type composite inflorescence form. Inflorescences arranged acropetally on a capitulum.

*Inflorescence longevity.*—Inflorescences last on the plant for 4 to 6 weeks and 2 to 3 weeks as a fresh cut flower, and more than 6 weeks as a dried cut flower. Inflorescences persistent.

*Natural flowering season.*—Natural flowering season is spring to fall. Plants flower continuously during this period. Inflorescences close when wet and open when dry.

*Quantity of inflorescences.*—About 1 to 3 inflorescences and about 2 to 5 flower buds per lateral branch.

*Inflorescence aspect.*—Flat to slightly cupped.

*Inflorescence diameter.*—About 4.4 to 5.7 cm.

*Inflorescence depth* (*height*).—About 1.6 to 2.3 cm.

*Disc diameter.*—About 1.6 to 2.1 cm.

*Fragrance.*—Slight honey.

*Involucral bracts.*—Appearance: Satiny. Texture: Papery. Aspect: Flat. Shape: Triangular. Margin: Entire. Apex: Acute. Base: Truncate. Length: About 0.8 to 1.9 cm. Width: About 2 to 5 mm. Color: When opening, upper surface: Towards apices, 66C; towards base, 62D. When opening, lower surface: Towards apices, 62A; towards base, 165D. Mature, upper surface: Towards apices, 66C to 62A; towards base, 158B. Mature, lower surface: Towards apices, 62A; towards base, 165D.

*Disc florets.*—Shape: Tubular with five lobes. Diameter: About 1 mm. Width: About 1 mm. Color: Immature: 154C. Mature: 24A.

*Peduncle.*—Length: About 10 to 17.5 cm. Aspect: Erect to about 25° from vertical. Strength: Moderately strong, brittle when young, inflorescences held erect above foliage. Color: 143C to 146D. Texture: Slightly rough; pubescent.

*Flower bud.*—Shape: Ovoid. Length: About 1.3 to 1.8 cm. Diameter: About 1.3 to 1.8 cm. Color: Towards apex, 70A; towards base, 156C.

*Androecium.*—Only present on disc florets. Stamen number: One per disc floret. Anther shape: Linear. Anther color: 23B. Amount of pollen: Moderate. Pollen color: 23A.

*Gynoecium.*—Present on disc florets. Pistil number: One per disc floret. Style length: About 3 mm. Style color: 23A to 23B. Stigma shape: Bilobate. Stigma color: 23A.

*Seed.*—Seed production has been observed.

Disease resistance: Susceptible to White Rust, causal agent *Albuto candida.*

It is claimed:

1. A new and distinct cultivar of Bracteantha plant named 'Florabella Pink', as illustrated and described.

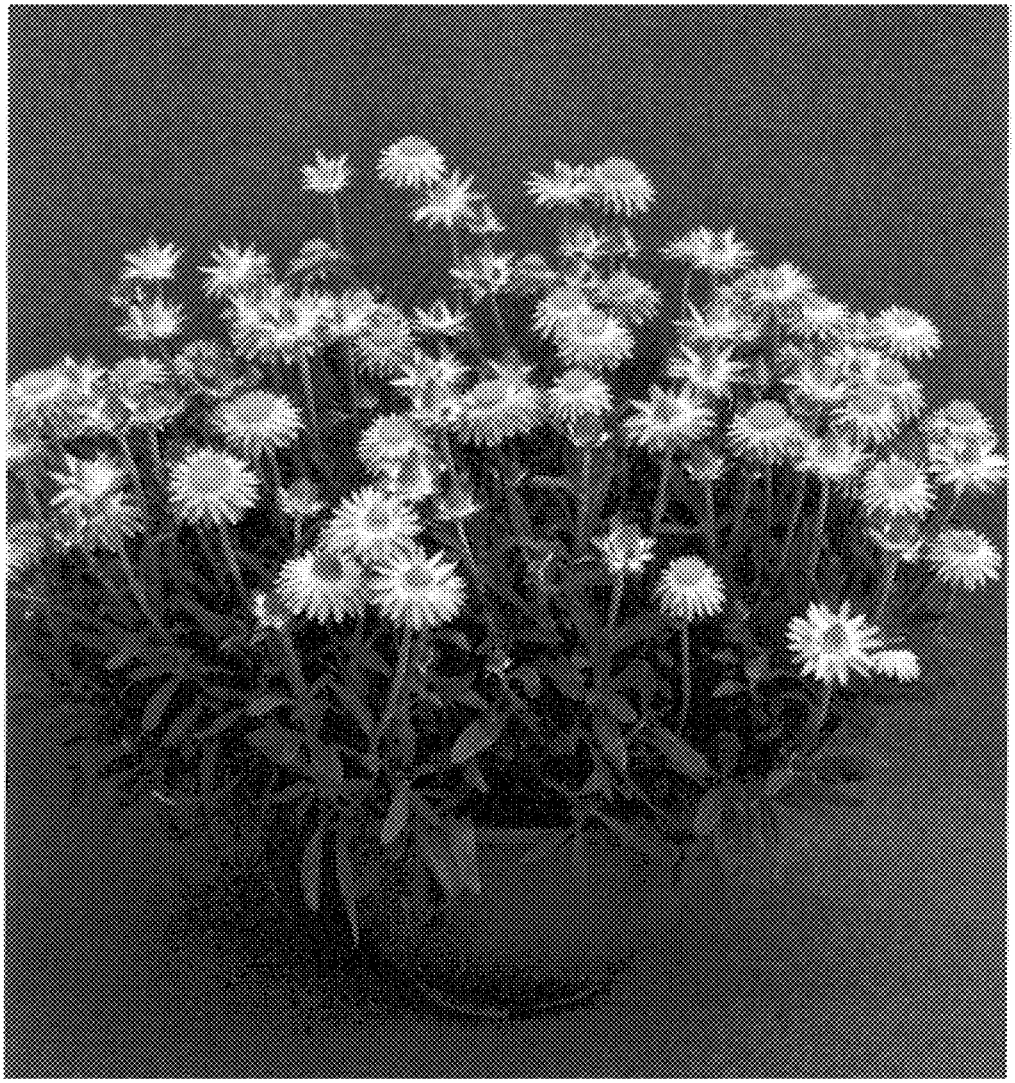

* * * * *